United States Patent
Bradshaw et al.

(10) Patent No.: US 8,153,390 B2
(45) Date of Patent: Apr. 10, 2012

(54) FRET-BASED BINDING ASSAY

(75) Inventors: James Michael Bradshaw, Palo Alto, CA (US); Joyce Karen Kwan, San Leandro, CA (US); Alden Er Hong Ling, Richmond (CA); David Shaw, San Francisco, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 164 days.

(21) Appl. No.: 12/773,797

(22) Filed: May 4, 2010

(65) Prior Publication Data

US 2010/0285503 A1    Nov. 11, 2010

Related U.S. Application Data

(60) Provisional application No. 61/175,692, filed on May 5, 2009.

(51) Int. Cl.
*C12Q 1/48* (2006.01)
(52) U.S. Cl. ........................................... 435/15
(58) Field of Classification Search .................. 435/15
See application file for complete search history.

(56) References Cited

U.S. PATENT DOCUMENTS

| | | |
|---|---|---|
| 2005/0064485 A1 | 3/2005 | Vogel |
| 2007/0202107 A1 | 8/2007 | Whyte et al. |
| 2007/0264678 A1 | 11/2007 | Vogel et al. |
| 2008/0138836 A1 | 6/2008 | Michaud et al. |

OTHER PUBLICATIONS

Kwan, J., et. al. "A fluorescence resonance energy transfer-based binding assay for characterizing kinase inhibitors: Important role for C-terminal biotin tagging of the kinase," Analytical Biochemistry, 2009, vol. 395, pp. 256-262.
Lebakken, C. S., et. al. "A Fluorescence Lifetime-Based Binding Assay to Characterize Kinase Inhibitors," Journal of Biomolecular Screening, 2007, vol. 12 (6), pp. 828-841.
Lebakken, C. S., et. al. "A one-step, mix-and-read, TR-FRET binding assay to characterize kinase inhibitors," The Leading European Event for Drug Discovery, 2008, p. 1, Abstract.
Li, Y, J., et. al. "Fluorescence detection techniques for protein kinase assay," Analytical and Bioanalytical chemistry, 2008, vol. 390 (8), pp. 2049-2057.
Zhang, W. X., et. al. "Time-resolved Forster resonance energy transfer assays for the binding of nucleotide and protein sustrates to p38 alpha protein kinase," Analytical Biochemistry, 2005, vol. 343, pp. 76-83.

*Primary Examiner* — Maryam Monshipouri
(74) *Attorney, Agent, or Firm* — David Chang; Brian L. Buckwalter

(57) ABSTRACT

The present invention provides for an assay that identifies kinase inhibitors by employing fluorescence resonance energy transfer in a competition binding approach.

3 Claims, 6 Drawing Sheets

A

B

A

B

A

B

C

D

FRET-BASED BINDING ASSAY

CROSS REFERENCE TO RELATED INVENTION

This application claims the benefit of priority of U.S. Provisional Patent Application Ser. No. 61/175,692, filed May 5, 2009, which is incorporated herein by reference in its entirety.

REFERENCE TO SEQUENCE LISTING

This application contains a Sequence Listing submitted as an electronic text file named "R0477APRO_ST25.txt", having a size in bytes of 2 kb, and created on 28 Apr., 2009. The information contained in this electronic file is hereby incorporated by reference in its entirety pursuant to 37 CFR §1.52 (e)(5).

FIELD OF THE INVENTION

This invention relates to competition binding assays that employ fluorescence resonance energy transfer (FRET). More particularly, the invention relates to kinase binding competition assays using FRET.

BACKGROUND OF THE INVENTION

The success of kinases as drug targets continues to motivate the development of new techniques to discover kinase inhibitors (1-3). Biochemical assays that show excellent sensitivity and are non-hazardous and low cost are needed (4). In addition, the different ways that inhibitors can bind to kinases (ATP-competitive, allosteric, inactive conformation, etc.) makes employing multiple approaches to characterize inhibitors advantageous (5, 6). For instance, in order to characterize inactive state inhibitors, methods that directly measure binding, rather than inhibition of activity, are desirable (1, 7, 8).

Several methods that have previously been employed to study direct binding of kinase inhibitors include isothermal titration calorimetry (ITC), surface plasmon resonance (SPR), and fluorescence competition (9-12). Each of these approaches has advantages as well as disadvantages. ITC can be performed in solution but is low through-put and requires a significant amount of material. SPR is higher-throughput but requires attachment of the kinase to a surface. A promising new method is a competition binding approach that employs time-resolved fluorescence resonance energy transfer (TR-FRET) (13, 14). In this method, a FRET donor such as europium cryptate is bound to the kinase via interaction with a purification tag (FIG. 1A). A FRET acceptor such as Alexa Fluor 647 is also bound to the kinase via attachment to a known inhibitor and serves as a tracer. If the 2 fluorophores are in proximity with the proper orientation, FRET will occur between them (FIG. 1A). Displacement of the tracer with an unlabeled inhibitor eliminates the FRET signal and provides a read-out on binding. This FRET-based competition assay has many potential advantages over competing methods; it is homogeneous, non-hazardous, high-throughput, and potentially has high sensitivity allowing for low usage of material and low cost.

FRET-based competition has previously been utilized in a few cases to characterize interaction of inhibitors with kinases. For instance, investigators have coupled europium via an AviTag-mediated, biotin-streptavidin interaction to the N-terminus of p38α kinase and proceeded to monitor inhibitor binding by competitive displacement of an Alexa Fluor 647-coupled p38α inhibitor (13). In another study, europium was coupled to kinases via an N-terminal GST/Anti-GST antibody interaction and inhibitor binding to a panel of kinases was studied by monitoring displacement of Alexa Fluor 647-tagged staurosporine (14). These studies have established the feasibility of using FRET-based competitive binding to characterize kinase inhibitors. However, there are many examples whereby binding both a tracer and europium does not result in a sufficient FRET signal. Hence, it would be useful to identify the most promising tagging strategies that reliably result in a robust FRET signal.

SUMMARY OF THE INVENTION

The present invention is based on the discovery that tagging kinases at their C-terminus using a biotin-streptavidin strategy produced the greatest FRET signal of the strategies examined. Specifically, when compared side-by-side with N-terminal tagging with either a GST/Anti-GST antibody or His/Anti-His antibody tag, C-terminal biotin tagging resulted in a 3-fold larger increase in signal.

Accordingly, the present invention provides for a method of screening for a substance that may be acting as a kinase inhibitor, said method comprising the steps of: providing a kinase enzyme that is fused at its C-terminus with an amino acid sequence that allows covalent attachment of biotin wherein said amino acid sequence does not comprise the AviTag™ sequence (SEQ ID NO:2); providing streptavidin that is labeled with a fluorescent donor moiety or a fluorescent acceptor moiety; providing a known kinase inhibitor wherein said known kinase inhibitor is labeled with a fluorescent acceptor moiety if said streptavidin in step b) is labeled with a fluorescent donor moiety, and wherein said known kinase inhibitor is labeled with a fluorescent donor moiety if said streptavidin in step b) is labeled with a fluorescent acceptor moiety; incubating said kinase enzyme, said streptavidin and said known kinase inhibitor in a reaction mixture in either the presence or absence of said substance; exposing the reaction mixture to light that allows fluorescence resonance energy transfer to take place and measuring fluorescence emission from the reaction mixture; wherein if the fluorescence emission measurement from the reaction mixture in the presence of said substance is different than the fluorescent emission measurement from the mixture in the absence of said substance, said substance may be acting as a kinase inhibitor.

The foregoing and other advantages and features of the invention, and the manner in which the same are accomplished, will become more readily apparent upon consideration of the following detailed description of the invention taken in conjunction with the accompanying examples, which illustrate exemplary embodiments.

DETAILED DESCRIPTION OF THE INVENTION

Definitions

Figure 1:
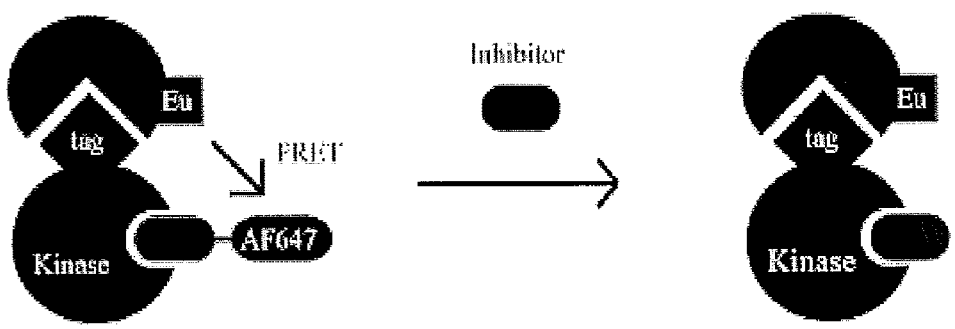
FIG. 1. The molecular basis of the FRET-based binding assay. (A) Schematic of the FRET assay. The europium (Eu) FRET donor is coupled to the kinase through an interaction with a purification tag such as GST, polyhistidine, or biotin. The Alexa Fluor 647 FRET acceptor is coupled to a known inhibitor of the kinase. Binding of Eu and AF 647 could result in FRET between the fluorophores if the fluorophores are in the proper orientation and in close enough proximity. Binding of an unlabeled inhibitor would displace Alexa Fluor 647 and result in a loss of FRET. (B) Domain structure of the protein constructs used in this study.
Figure 1:
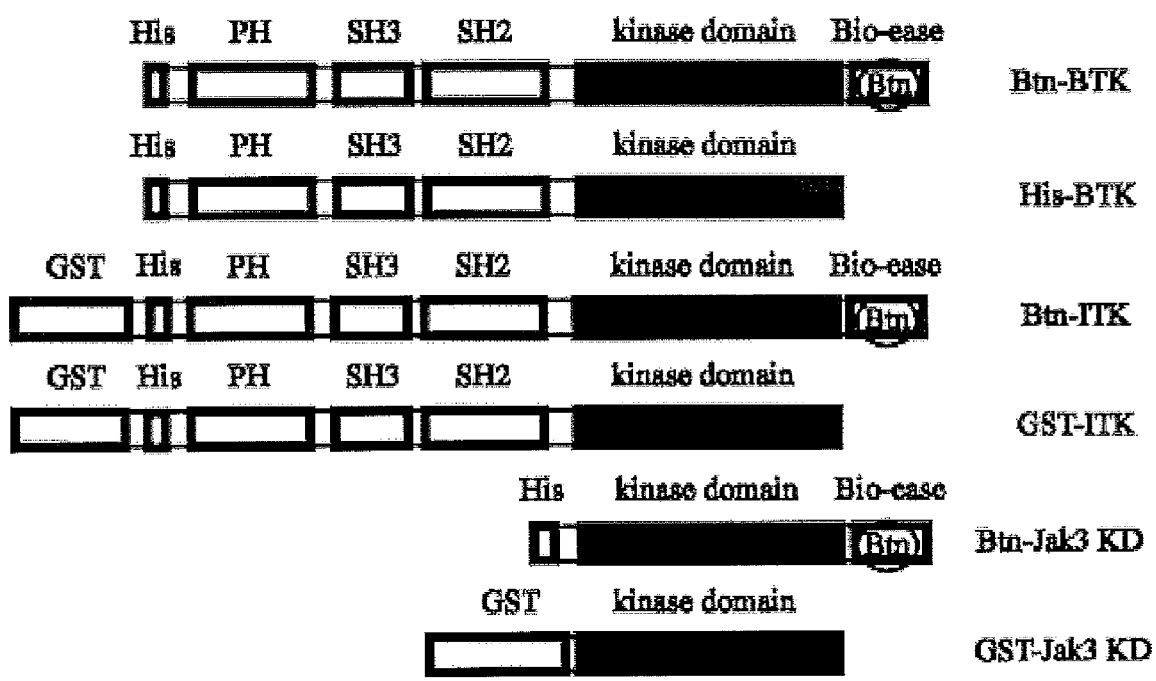

Generally, the nomenclature used herein and many of the fluorescence, luminescence, computer, detection, chemistry, and laboratory procedures described herein are commonly employed in the art. Standard techniques are generally used for chemical synthesis, fluorescence or luminescence monitoring and detection, optics, molecular biology, and computer software and integration. Chemical reactions, cell assays, and enzymatic reactions are typically performed according to the manufacturer's specifications where appropriate. See, generally, Lakowicz, J. R. *Topics in Fluorescence Spectroscopy*, (3 volumes) New York: Plenum Press (1991), and Lakowicz, J. R. *Emerging applications of florescence spectroscopy to cellular imaging: lifetime imaging, metal-ligand probes, multi photon excitation and light quenching*, Scanning Microsc. Suppl. Vol. 10 (1996) pages 213-24, for fluorescence techniques; Sambrook et al., *Molecular Cloning: A Laboratory Manual*, 2ed. (1989) Cold Spring Harbor Laboratory Press, Cold Spring Harbor, N.Y., for molecular biology methods; *Cells: A Laboratory Manual*, $1^{st}$ edition (1998) Cold Spring Harbor Laboratory Press, Cold Spring Harbor, N.Y., for cell biology methods; and *Optics Guide* 5 Melles Griot® Irvine Calif., and *Optical Waveguide Theory*, Snyder & Love (published by Chapman & Hall) for general optical methods, all of which are incorporated herein by reference.

General methods for performing a variety of fluorescent or luminescent assays on luminescent materials are known in the art and are described in, e.g., Lakowicz, J. R., Topics in Fluorescence Spectroscopy, volumes 1 to 3, New York: Plenum Press (1991); Herman, B., Resonance Energy Transfer Microscopy, in Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361; and Bernard Valeur, "Molecular Fluorescence: Principles and Applications" Wiley VCH, 2002. Guidance in the selection and use of specific resonance acceptor moieties is available at, for example, Berlman, I. B., Energy transfer parameters of aromatic compounds, Academic Press, New York and London (1973), which contains tables of spectral overlap integrals for the selection of resonance energy transfer pairs. Additional information sources include the Molecular Probes Catalog (2003) and website; and Tsien et al., 1990 Handbook of Biological Confocal Microscopy, pp. 169-178. Instruments useful for performing FP and/or RET and TR-RET applications are available from Tecan Group Ltd. (Switzerland) (Ultra, Ultra 384, Ultra Evolution); Perkin-Elmer (Boston, Mass.) (Fusion, EnVision, Victor V, and ViewLux), Amersham Bioscience (Piscataway, N.J.) (LeadSeeker); and Molecular Devices Corporation (Sunnyvale, Calif.) (Analyst AD, GT, and HT).

The term "FRET" means "fluorescence resonance energy transfer" or "Forster resonance energy transfer", and refers to the radiationless transmission of an energy quantum from its site of absorption (the donor) to the site of its utilization (the acceptor) in a molecule, or system of molecules, by resonance interaction between donor and acceptor species, over distances considerably greater than interatomic, without substantial conversion to thermal energy, and without the donor and acceptor coming into kinetic collision. A donor is a moiety that initially absorbs energy (e.g., optical energy or electronic energy). A luminescent metal complex as described herein can comprise two donors: 1) an organic antenna moiety, which absorbs optical energy (e.g., from a photon); and 2)

a lanthanide metal ion, which absorbs electronic energy (e.g., transferred from an organic antenna moiety).

The term "acceptor" refers to a chemical or biological moiety that accepts energy via resonance energy transfer. In FRET applications, acceptors may re-emit energy transferred from a donor fluorescent or luminescent moiety as fluorescence and are "fluorescent acceptor moieties." As used herein, such a donor fluorescent or luminescent moiety and an acceptor fluorescent moiety are referred to as a "FRET pair." Examples of acceptors include coumarins and related fluorophores; xanthenes such as fluoresceins and fluorescein derivatives; fluorescent proteins such as GFP and GFP derivatives; rhodols, rhodamines, and derivatives thereof; resorufins; cyanines; difluoroboradiazaindacenes; and phthalocyanines Acceptors, including fluorescent acceptor moieties, can also be useful as fluorescent probes in fluorescence polarization assays.

The terms "label" or "labeled" refer to the inclusion of a luminescent metal complex or a fluorescent acceptor moiety on a molecule or substance.

The term "covalent" refers to a form of chemical bonding that is characterized by the sharing of pairs of electrons between atoms, or between atoms and other covalent bonds. Covalent attachment of biotin occurs on a particular lysine residue of a peptide sequence. Biotinylation can occur either "in vivo", whereby intracellular biotinylation enzymes are able to recognize the amino acid sequence to attach the biotin molecule, or "in vitro" whereby biotinylation occurs through the use of the enzyme biotin ligase (BirA) and ATP.

In the present invention, we sought to discover new factors that would lead to a more reliable and improved FRET-based competition binding assay for kinases. We evaluated how the FRET signal for BTK, ITK, and Jak3 was affected by different purification tags located at either the N-terminus or C-terminus of the kinase. It was discovered that C-terminal biotinylation was an optimal tagging strategy. Specifically, coupling of a FRET acceptor to a kinase C-terminus via biotin resulted in a significantly larger FRET signal compared to other strategies. This discovery facilitated the development of a binding assay with either kinase or tracer concentration in the tens of picomolar range, the lowest concentrations yet reported for this assay. The strong sensitivity of the assay allowed for the potency evaluation of low nanomolar BTK inhibitors. C-terminal biotinylation also proved reliable in generating a FRET signal for all of the kinases investigated.

Figure 4:
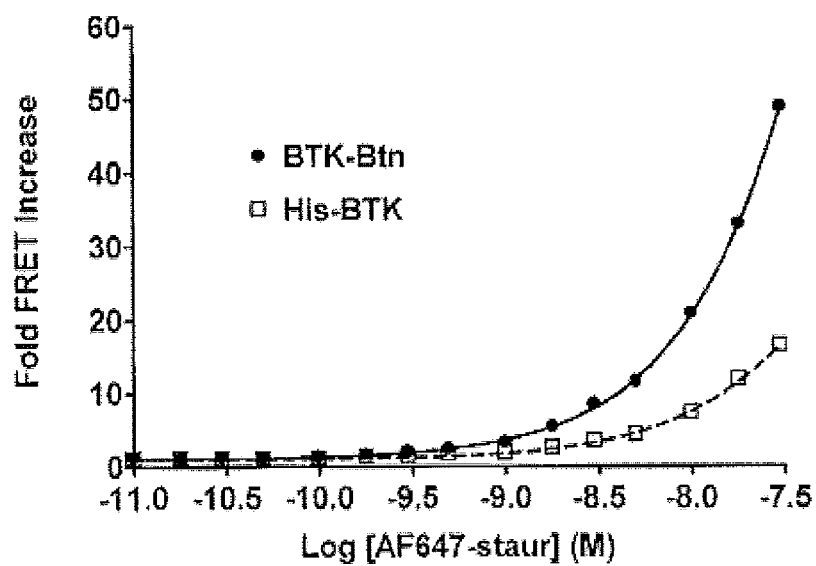
FIG. 4. Comparison of the Fold FRET Increase of Btn-BTK and His-BTK. (A) Shown is the Fold FRET Increase as a function of AF647-staur at 5 nM BTK. (B) Shown is the Fold FRET Increase as a function of TR 178 at 5 nM BTK. In both (A) and (B), data for Btn-BTK is shown in solid squares and for His-BTK is shown in open circles. Error bars represent the standard deviation of multiple data points. Solid lines represent the nonlinear least squares best fit to a sigmoidal dose-response function.
Figure 4:
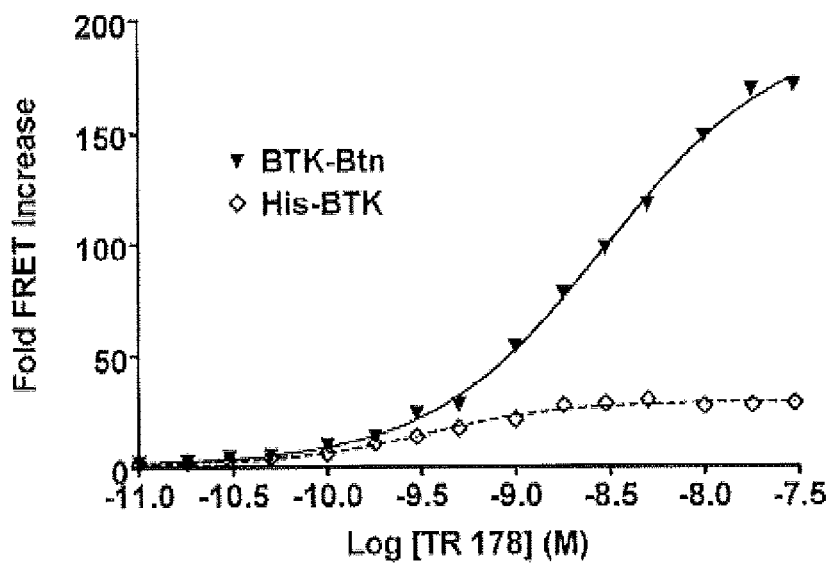
Figure 5:
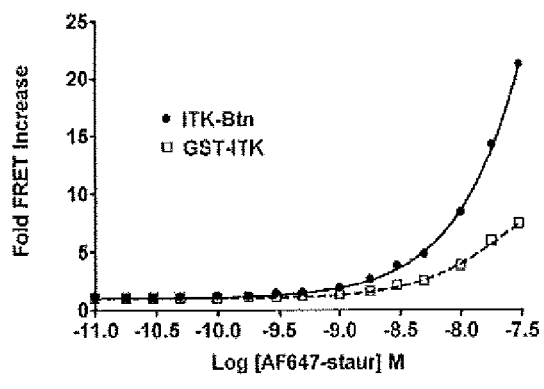
FIG. 5 Assessment of the Fold FRET increase for ITK and Jak3 KD. (A) Shown is the Fold FRET Increase for ITK-Btn and GST-ITK as a function of AF647-staur. (B) Shown is the Fold FRET Increase for ITK-Btn and GST-ITK as a function of TR 236. (C) Shown is the Fold FRET Increase for Jak3 KD-Btn and GST-Jak3 KD as a function of AF647-staur. (D) Shown is the Fold FRET Increase for Jak3 KD-Btn and GST-Jak3 KD as a function of TR 236. For all data sets, error bars represent the standard deviation of multiple data points. Solid lines represent the nonlinear least squares best fit to a sigmoidal dose-response function.
Figure 5:
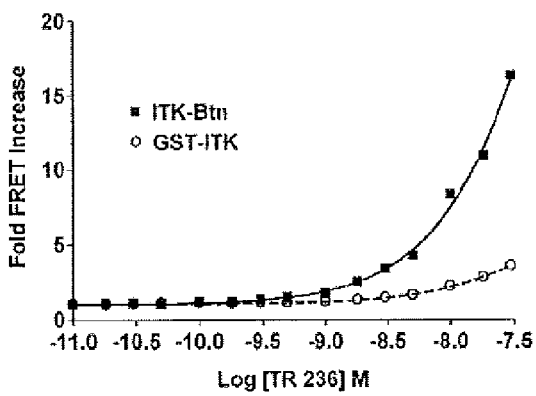
Figure 5:
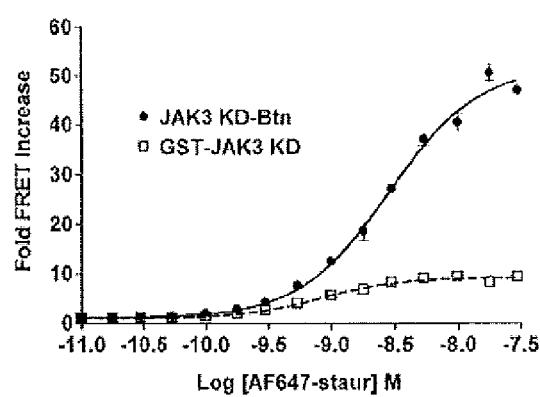
Figure 5:
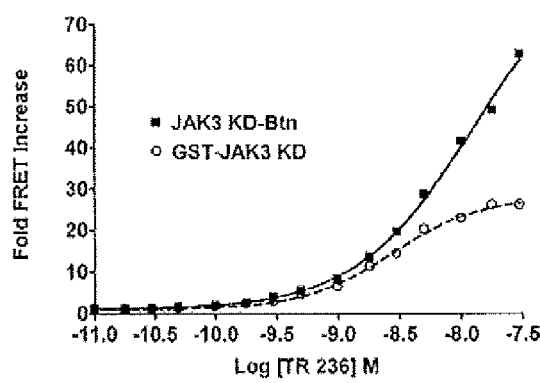

In this study, we compared the maximum FRET signal obtained with C-terminal biotinylation side-by-side with that obtained using an N-terminal His or GST tag. (See FIG. 4 and FIG. 5). In 5 out of the 6 combinations of kinase and tracer examined, C-terminal biotinylation provided a 3-fold or greater maximal FRET signal compared with the N-terminal tag (Table 2). In the 6$^{th}$ example, the C-terminal biotin tag provided a 2.4-fold greater maximal FRET signal (Table 2). The largest FRET signal change observed here was the 171-fold increase observed for the binding of BTK-Btn to Tr 178 (FIG. 4B). Prior to this finding, the largest FRET increase reported in the literature for a comparable assay was ~30-fold for the binding of an Alexa Fluor 647-labeled tracer to p38α kinase (13). Hence, the investigation presented here has uncovered a new tagging strategy to maximize the signal change in FRET, and this strategy might be generally applicable to many kinases.

Figure 3:
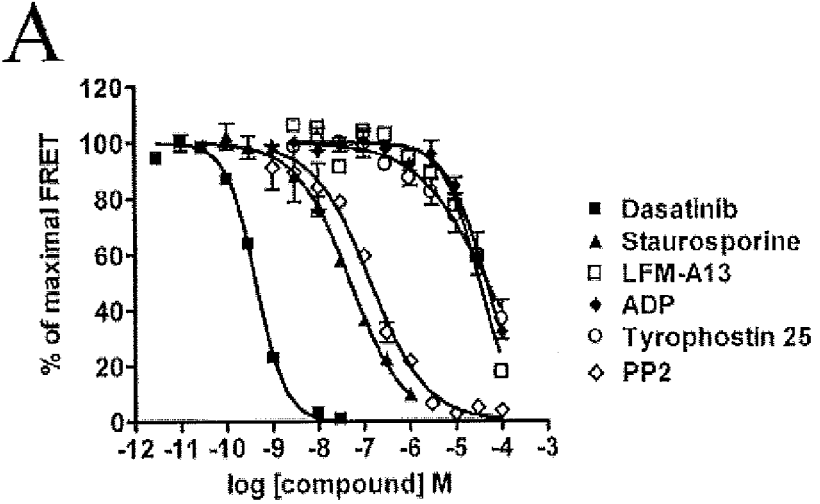
FIG. 3. Potency of BTK inhibitors using the FRET competition assay and an enzymatic inhibition assay. (A) Potency of BTK inhibitors assessed using the FRET competition assay. Shown is the percent of maximal FRET as a function of compound concentration. Data for dasatinib are shown in closed squares, staurosporine in closed triangles, LFM-A13 in open squares, ADP in closed diamonds, tyrphostin 25 in open circles, and PP2 in open diamonds. Solid lines represent the nonlinear least squares best fit to a sigmoidal dose-response function. Here, [Btn-BTK]=0.5 nM, [Eu-strept]=0.5 nM, and [AF647-staur]=2.5 nM. (B) Potency of BTK inhibitors using an enzymatic BTK inhibition assay. Shown is the percent of maximal activity as a function of compound concentration. Solid lines represent the nonlinear least squares best fit to a sigmoidal dose-response function. Here, [His-BTK]=5 nM. (C) Effect of [Btn-BTK] on the potency of dasatinib in the FRET competition binding assay. Shown is the Fold FRET Increase as a function of dasatinib. Data were collected at [Btn-BTK]=0.5 nM (solid squares), [Btn-BTK]= 0.25 nM (open triangles), and [Btn-BTK]=0.12 nM (open circles). Solid lines represent the nonlinear least squares best fit to a sigmoidal dose-response function.
Figure 3:
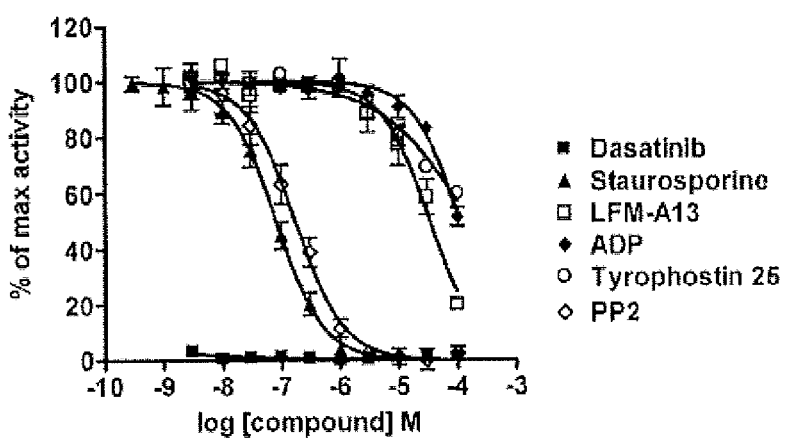
Figure 3:
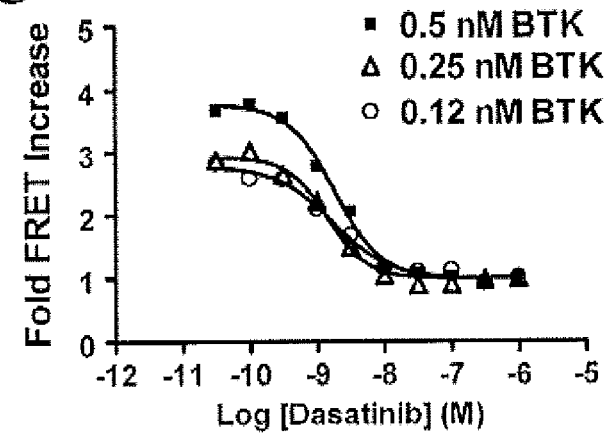

Benefits derived from maximizing the FRET signal include enabling potency measurement of strong inhibitors and minimizing use of reagents in high-throughput screening. More potent inhibitors can be measured because the higher FRET signal allows a lower enzyme concentration to be employed in the assay, and the required enzyme concentration is well known to determine the lower limit of potency in IC50-type assays. For BTK, the optimized TR-FRET competition assay employed only 50 pM of BTK-Btn. In contrast, the BTK enzymatic assay required 5 nM enzyme. Hence, the FRET assay increased the measurable window of potency for BTK by 100-fold. The potency determination of dasatinib provided a demonstration of the value of the FRET-based competition assay in characterizing strong inhibitors (FIG. 3C).

Maximizing the signal change in the FRET-based competition assay using C-terminal biotinylation will increase the applicability of the assay in general. It is already clear that the assay is valuable for kinases that have no known substrate or that demonstrate low intrinsic activity. In addition, the FRET-based assay is very useful for characterizing inhibitor that bind specifically to an inactive conformation of the kinase. These inhibitors can be difficult to characterize using enzymatic approaches but are generally attractive because they often show good selectivity (7, 8, 21). Examples of this class of inhibitor include Gleevec (an Abl inhibitor) and Lapatinib (an EGFR/HER2 inhibitor) (22, 23).

This is the first report describing the use of a BioEase™ (SEQ ID NO:1) type of biotin-tagging system in application to FRET-based kinase competition experiments. A prior report utilized an AviTag™ (SEQ ID NO:2) for site specific incorporation of biotin into the kinase (13). The BioEase™ tagging system appears to have advantages compared with the AviTag™ approach. Most significantly, the BioEase™ tagging system enables incorporation of biotin within a baculovirus insect cell expression whereas the AviTag™ was not found to be biotinylated in insect cells. Since many kinases are purified from insect cells, the BioEase™ tag provides a very straight-forward approach to biotinylating kinases for FRET-based competition studies.

There are other factors in addition to the C-terminal placement of the tag that might make C-terminal biotinylation advantageous for FRET-based competition studies. For instance, the smaller size of the biotin-streptavidin pair compared to the larger antibody-mediated interactions may be more optimal for producing FRET. The biotin-streptavidin interaction also seems to be stronger than some tag/anti-tag antibody interactions, and tight binding between the FRET donor and tag is necessary if only tens of picomolar enzyme and tag are employed in the assay. Another factor that may contribute to the strong FRET signal is the fact that streptavidin forms a tetramer with 4 biotin binding sites; the tetramer should bring multiple kinase molecules into proximity which may increase FRET. Whether each of these factors is important to generating a maximal FRET signal is currently unknown. In future investigations, it would be enlightening to explore which of these factors is important for providing the superior FRET signal provided by C-terminal biotinylation

EXAMPLES

Materials and Methods
Materials

Biotinylated (Bioease) BTK, ITK, JAK3, and glutathione S-transferase (GST) tagged ITK were produced as described below. Polyhistidine (His) tagged BTK and GST tagged Jak3 kinase domain were from Invitrogen (Carlsbad, Calif.). See FIG. 1B for the domain organization of the protein constructs used. Alexa Fluor 647-Staurosporine, Kinase Tracer 178, and Kinase Tracer 236 were from Molecular Probes/Invitrogen (Eugene, Oreg.); Kinase Tracer 178 and 236 are kinase inhibitors of undisclosed identity coupled to Alexa Fluor 647.

LANCE europium-W1024 streptavidin, LANCE europium W1024 Anti-GST antibody, and LANCE europium W1024 anti-His antibody were from PerkinElmer (Waltham, Mass.). DMSO was from J.T. Baker (Phillipsburg, N.J.). The assay buffer used was 20 mM HEPES pH 7.15 (from Cellgro, Manassas, Va.), 0.1 mM dithiothreitol (DTT), 0.5 mg/mL bovine serum albumin (BSA), and 10 mM $MgCl_2$ (all from Sigma-Aldrich, St. Louis, Mo.).

Purification of Biotin-tagged Kinases

Incorporation of the BioEase™ tag for BTK, ITK, and Jak3 kinase domain was accomplished using the BioEase™ Gateway Biotinylation System (Invitrogen). The BioEase™ tag represents amino acid residues 524-595 of *Klebsiella pneumoniae* oxalacetate decarboxylase α subunit and facilitates in situ biotinylation within the expression cells at lysine residue 561 of oxalacetate decarboxylase. The DNA sequence that confers the BioEase™ tag was PCR amplified from pcDNA6/BioEase-DEST (Invitrogen) and inserted into a Gateway adapted version of pVL1392 (Pharmingen). This new vector, pVL101-cBioEase, confers a C-terminal BioEase™ tag fusion protein to appropriately designed pENTR constructs of BTK, ITK and Jak3 kinase domains. The resulting ORF expresses an N-terminal 6×His tag followed by the gene-of-interest and a C-terminal BioEase™ tag. Baculovirus was generated by co-transfection with BaculoGold Bright linearzied baculovirus DNA (Pharmingin). Subsequent expansion and passages of baculovirus were carried out until a high-titre P3 stock was obtained for fermentation purposes. For expression, Sf-9 cells were infected at $1.2 \times 10^6$ cells/ml with virus at multiplicity of infection of 0.1 to 0.5. Cultures were incubated at 27° C. for 2-3 days, harvested at 3000 RPM in a tabletop centrifuge, and stored at −80° C. Cells were lysed in extraction buffer (20 mM Hepes pH 8.0, 500 mM NaCl, 5 mM β-mercaptoethanol, 5 mM imidazole, 0.2% Tween-20, 10 U/ml Benzonase, and 10% glycerol) and insoluble material was pelleted. For BTK, soluble material was applied to a His Trap FF column, washed with 50 mM Hepes pH 8.0, 10% glycerol, 1 mM DTT, 20 mM imidazole and 300 mM NaCl, and eluted with the same buffer except 300 mM imidazole. Eluted material was applied to a Superdex 200 26/60 column equilibrated in 50 mM Hepes pH 7.6, 5% glycerol, 2 mM DTT, 250 mM NaCl, and 10 mM MgC12 at 2 ml/min. For Jak3 kinase domain, purification was accomplished using an IMAC column (in extraction buffer minus 10 U/ml Benzonase) followed by Superdex 75 26/60 (in a buffer of 50 mM Hepes pH 8.0, 500 mM NaCl, 5 mM DTT, 20% glycerol). For ITK, material was applied to a NiNTA column equilibrated in 25 mM Tris pH 8.0, 500 mM NaCl, 20 mM imidazole, 10% glycerol, 0.1% Brj-35, and 5 mM β-mercaptoethanol. Material was eluted in the same buffer plus 125 mM imidazole. ITK was next concentrated to 200 μL using an AmiconUltra centrifugal filter with MWCO 50 kDa. Resulting material was injected onto a Superdex 200 GL 10/300 column equilibrated in 50 mM Tris pH 7.5, 150 mM NaCl, 0.5 mM EDTA, 2 mM DTT, and 10% glycerol. ITK-containing fractions were identified using SDS-PAGE, pooled, and concentrated to 2 mg/ml. All kinases were stored at −80° C.

TR-FRET Measurements

All TR-FRET experiments were performed in a final volume of 20 uL in a black 384-well polystyrene low volume (20 uL) assay plate. Solutions were incubated at room temperature for one hour under an amber plate cover prior to data collection. A Velocity11 Bravo pipetting robot (Agilent, Santa Clara, Calif.) was used to ensure a thorough and even mixing of solutions. TR-FRET was detected with a Pherastar fluorometer from BMG LABTECH (Offenburg, Germany) with excitation at 337 nM and detection of emission at both 620 and 665 nM. Optimal fluorescence detector height was determined by calibrating against the well with the highest predicted signal.

For each kinase construct, the molar ratio of kinase to europium tag that provided the highest FRET signal was experimentally determined and kept fixed through subsequent experiments. It was ascertained that a 5:1 enzyme to tag ratio was optimal for His-BTK, GST-ITK, GST-Jak3 KD. A ratio of 5:1 enzyme to tag was also optimal between biotin-tagged kinase and the europium-coupled streptavidin tetramer.

Compound $IC_{50}$ Experiments

For IC50 experiments, compounds to be tested were diluted in half-log intervals with DMSO using a Biomek 2000 pipetting robot (Beckman Coulter, Fullerton, Calif.). The first and last columns were filled with DMSO to serve as negative and positive controls. Following dilution in a 96-well plate format, the solutions were transferred to a clear 384-well polypropylene V-bottom plate in a volume of 25 uL.

For compound screening, BTK-Btn and AF647-staur were first incubated together at 5.5 nM and 33 nM, respectively, for one hour on ice. The solution was then diluted to a concentration of 0.55 nM enzyme and 3.33 nM tracer. After a five minute incubation at room temperature, the enzyme tracer mix was distributed in 18 uL aliquots in duplicates into an assay plate. The Velocity11 Bravo pipetting robot was used to transfer 2 uL from the compound plate to the corresponding wells in the assay plate. Here, the final assay concentrations were 0.5 nM enzyme and 3 nM tracer with different 10 compound concentrations spaced at half log intervals. For titrations with dasatinib, the enzyme concentration in the procedure described above was also reduced 2-fold and 4-fold so that the final BTK-Btn concentration was 0.5 nM, 0.25 nM, and 0.12 nM.

Enzymatic Assay for BTK

BTK activity toward a peptide substrate (sequence: 5-FAM-EAIYAAPFAKKK) was measured using the Caliper Desktop Profiler (Caliper Life Sciences, Hopkinton, Mass.). Phosphorylated peptide was separated from substrate using a capillary electrophoresis system embedded in the Desktop Profiler. For evaluation of compound potency, compounds were diluted in DMSO in half-log intervals. Compounds (10 μL) were mixed with 26 μL of purified full length BTK (final concentration of 5 nM) in Caliper buffer (100 mM Hepes pH 7.5, 10 mM $MgCl_2$, 1 mM DTT, 0.004% Tween-20, and 0.003% Brij-35) and incubated for 10 minutes at room temperature. The kinase reaction was initiated by the addition of 10 μL of substrate cocktail such that the final concentration was 100 μM ATP and 1.5 μM peptide substrate. After 15 minutes at 30° C., the kinase reaction was terminated by the addition of 45 uL of 20 mM EDTA. IC50 values are interpolated from a graph of inhibitor concentration versus percent inhibition. Percent inhibition is calculated based on the uninhibited enzyme rate. Data were fitted to a 2 parameter dose response curve to determine the IC50.

Tracer Titration Experiments

For tracer titration experiments, 5 nM enzyme was employed unless noted otherwise. The tracer in the experiment was serially diluted with DMSO from a 1 uM stock in quarter-log intervals from 300 nM to 0.1 nM for a total of 16 tracer concentrations including a 0 nM DMSO-only condition. Following tracer dilution, the enzyme was distributed in 18 uL aliquots into 32 wells of an assay plate. This was followed by addition and thorough mixture of 2 uL of each of the tracer dilution conditions. Solutions were incubated at room temperature for one hour under an amber plate cover prior to data collection.

Data Fitting

Raw data from FRET experiments were collected as the FRET signal ratio (FSR), which is $10,000 \times (S_{665\ nM}/S_{620\ nM})$ where S is the magnitude of the emission signal from the corresponding wavelength. From these data, the fold FRET increase is calculated as $FSR_{target}/FSR_{negative\ control}$ where $FSR_{negative\ control}$ is the FRET signal observed with tracer and europium but in the absence of kinase. In some cases, the FRET signal is expressed as "% of maximal FRET" where 100% is the maximal fold FRET increase and 0% is the baseline FRET level.

Fitting of dose-response curves was performed using GraphPad Prism4. For determination of compound potency, the percentage of maximal FRET was first determined by the following equation: $100 \times [(FSR_{target} - FSR_{negative\ control})/(FSR_{positive\ control} - FSR_{negative\ control})]$. Data were then plotted against logarithm$_{10}$ of compound concentration (M), and fit to sigmoidal dose-response curves with variable slope and top and bottom constraints of 100 and 0, respectively. For tracer titration experiments, data were also fit to a sigmoidal dose response function using GraphPad Prism4. If a plateau in the Fold FRET increase was obtained, EC50s values were determined.

Results

TR-FRET Assay with BTK-Btn

We first set out to develop a competition binding assay for Bruton's tyrosine kinase (BTK) using detection by TR-FRET. An optimized assay would provide us the following: 1) a method to directly evaluate the potency of compounds for both the active and inactive conformation of BTK, 2) an ability to determine the Kd of very potent, sub-nanomolar compounds, and 3) a high-throughput assay that made minimal use of reagents. A construct of BTK was constructed that contained a 72 residue BioEase™ tag at the C-terminus (BTK-Btn). The BioEase™ tag facilitated coupling of a biotin molecule to a specific lysine residue within the tag (15). It was confirmed by mass spectrometry that indeed >90% of purified BTK-Btn was coupled to biotin.

Figure 2:
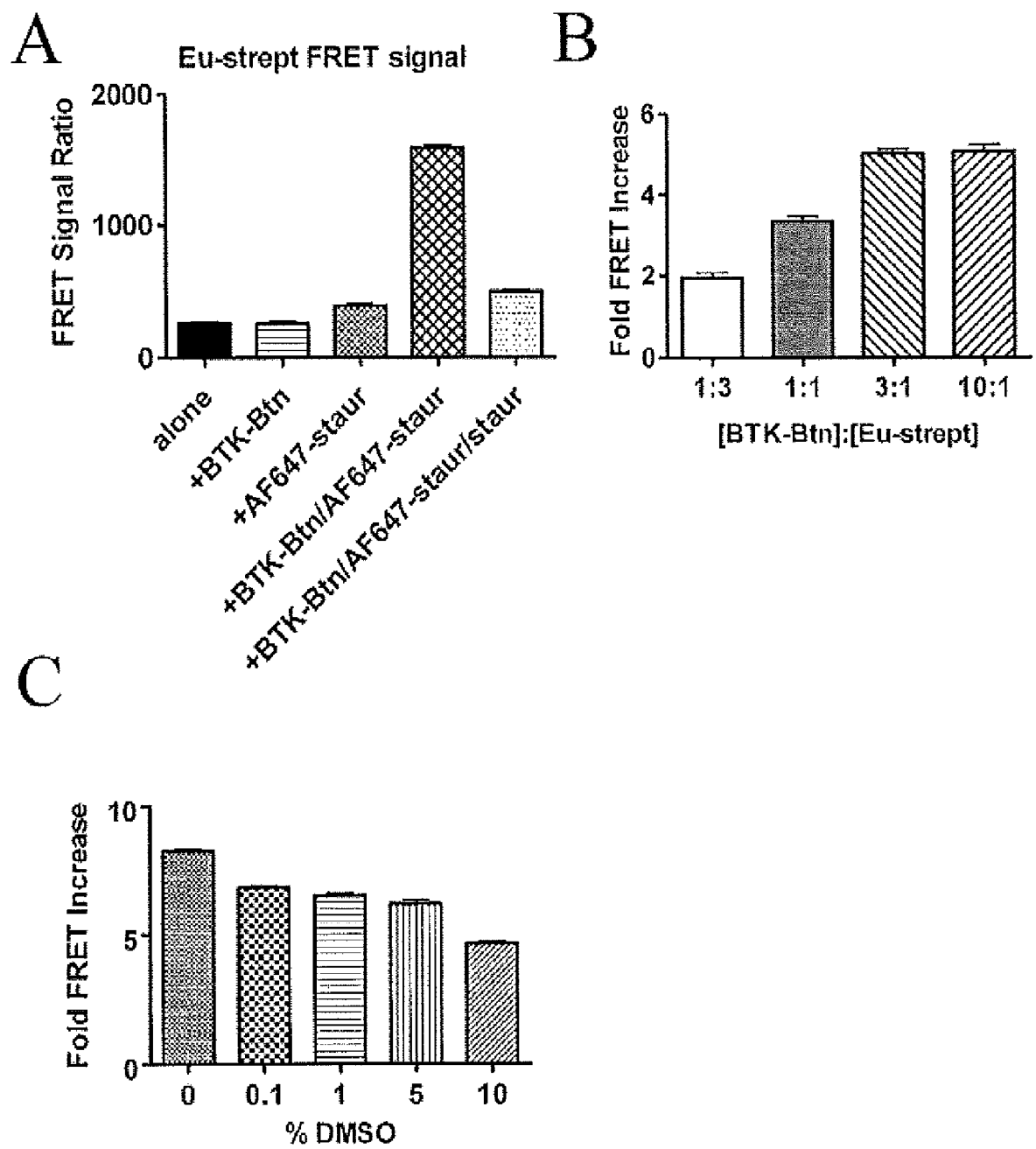
FIG. 2. Development of the FRET-based assay for BTK-Btn and AF647-staur. (A) Shown is the FRET Signal ratio $(10,000 \times (S_{665\ nM}/S_{620\ nM}))$ where S is the magnitude of the emission signal at that wavelength) for 10 nM Eu-strept in the absence or presence of various combinations of 10 nM BTK-Btn, 10 nM AF647-staur, and 10 µM unlabeled staurosporine (staur). (B) Optimization of the FRET signal for the ratio of BTK-Btn:Eu-strept. Shown is the Fold FRET increase using 1 nM AF647-staur, 1 nM Eu-strept, and either 0.3, 1, 3, or 10 nM BTK-Btn. (C) Effect of DMSO concentration on the Fold FRET Increase. Here, Btn-BTK=0.5 nM, Eu-strept=0.5 nM, and AF647-staur=2.5 nM.

Following purification, it was investigated whether BTK-Btn could be utilized for a TR-FRET-based inhibitor binding assay. For these initial studies, strepatvidin-coupled europium cryptate (Eu-strept) and the tracer Alexa Fluor 647-coupled staurosporine (AF647-staur) were employed. Eu-strept was incubated with either BTK-Btn, AF647-staur, or both and the FRET signal was monitored (FIG. 2A). It was ascertained that incubation of either BTK-Btn or AF647-staur individually with Eu-strept resulted in the same level of background signal as Eu-strept alone. However, incubation of BTK-Btn, AF647-staur, and Eu-strept together resulted in a 5-fold greater signal. The increase in FRET was eliminated by incubation with unlabeled staurosporine, indicating the FRET signal was dependent upon binding of AF647-staur.

In order to optimize the TR-FRET signal, the ratio of BTK-Btn to Eu-strept was varied (FIG. 2B). The maximal signal was obtained with BTK-Btn in excess of Eu-strept (FIG. 2B, Also See Material and Methods). Furthermore, since kinase inhibitors are typically dissolved in DMSO, the assay was also optimized with respect to DMSO. Varying the DMSO between 0% and 10% revealed that 10% DMSO caused only a modest, 2-fold reduction in the FRET signal (FIG. 2C), enabling the final assay conditions in the competition binding studies to contain 10% DMSO.

Compound Potency with BTK-Btn

The TR-FRET assay was next utilized to determine the potency of BTK inhibitors. We chose 6 inhibitors from the literature (dasatinib, staurosporine, LFM-A13, ADP, tyrphostin 25, and PP2) (16-18), and the FRET signal was measured at 10 different compound concentrations to generate an IC50 curve (FIG. 3A). As expected, the compounds demonstrated a range of potency including $IC_{50}=0.14\pm0.04$ μM for PP2 and $IC_{50}=0.050\pm0.007$ μM for staurosporine (See FIG. 3A and Table 1). We compared the potency of compounds using the TR-FRET assay to the potency measured using a BTK enzymatic activity assay. Specifically, we measured the activity of BTK (without the biotin tag) towards a peptide substrate using a capillary-based separation method (See Material and Methods). It was determined that compound IC50s measured in the BTK enzyme activity were comparable to those measured in the TR-FRET competition binding assay (FIG. 3B, Table 1).

TABLE 1

Potency of BTK inhibitors measured by FRET competition and enzyme inhibition assays

| compound | FRET IC$_{50}$ (μM) | FRET n$_H$ | Enzyme IC$_{50}$ (μM) | Enzyme n$_H$ |
|---|---|---|---|---|
| dasatinib | 0.0006 ± 0.0001 | 1.3 ± 0.1 | nd | nd |
| staurosporine | 0.050 ± 0.007 | 0.8 ± 0.1 | 0.082 ± 0.014 | 1.1 ± 0.1 |
| LFM-A13 | 33 ± 10 | 1.1 ± 0.2 | 34 ± 7 | 1.1 ± 0.1 |
| ADP | 46 ± 7 | 1.0 ± 0.1 | >100 | 1.0 ± 0.1 |
| Tyrphostin 25 | 48 ± 15 | 0.6 ± 0.1 | >100 | 0.6 ± 0.1 |
| PP2 | 0.14 ± 0.04 | 0.8 ± 0.1 | 0.17 ± 0.03 | 1.1 ± 0.1 | n$_H$, hill slope of dose response curve. nd, not determined.

The potency of dasatinib was too strong to be accurately measured using the BTK enzyme assay since the apparent IC$_{50}$ of the dose-response curve was below the minimal concentration of enzyme required in the experiment which was 5 nM (FIG. 3B). It was hypothesized that the sensitivity of the TR-FRET assay would allow a lower [BTK-Btn] to be employed, permitting determination of the potency. IC$_{50}$ curves for dasatinib were collected in the TR-FRET assay using 0.5, 0.25, and 0.12 nM BTK-Btn. The signal was sufficiently strong at all concentrations to collect an IC$_{50}$ curve (FIG. 3C). Analysis of the dose-response revealed IC$_{50}$ values of 1.83±0.07 nM, 1.42±0.05 nM, and 1.72±0.06 nM for the 0.5, 0.25, and 0.12 nM BTK-Btn concentrations, respectively. The fact that the IC$_{50}$s were greater than [BTK-Btn] in these experiments, together with the lack of variation in IC$_{50}$ with different [BTK-Btn], suggest that the measured IC$_{50}$s reflect the potency of dasatinib for BTK-Btn.

Comparison of TR-FRET Between BTK-Btn and His-BTK

We next investigated the maximal increase in FRET that could be obtained upon binding of AF647-staur to BTK-Btn. Incrementally increasing AF647-staur from 0.01 nM to 30 nM at 5 nM BTK-Btn resulted in a 49-fold increase in FRET (FIG. 4A). However, the dose-reponse curve did not plateau at 30 nM AF647-staur, preventing an estimate of the potency of AF647-staur for BTK-Btn (but suggesting that the $K_d$ was greater than 10 nM). This finding is consistent with the IC50 for staurosporine described above and a reported affinity of staurosporine for BTK of 36±9 nM (17).

It has previously been reported that a TR-FRET signal for kinases can be obtained by coupling europium via an N-terminal GST/Anti-GST antibody interaction (14). The BTK constructs employed here have an N-terminal His tag (See FIG. 1B), and an antibody to couple europium via a His tag is commercially available. Hence, we determined the maximal FRET using His-BTK coupled to europium. The concentration of AF647-staur was increased from 0.01 nM to 30 nM, and a maximal FRET increase of 16-fold at 30 nM AF647-staur was observed (FIG. 4A), which was 3-fold less than shown by BTK-Btn. Like BTK-Btn, the signal did not plateau for His-BTK at the highest AF647-staur examined.

We next explored if a difference in maximal FRET between BTK-Btn and His-BTK would be observed with a tracer other than AF647-staur. Several kinase inhibitors coupled to Alexa Fluor 647 were studied (See Material and Methods) and attention focused on tracer 178 (TR 178). Using BTK-Btn, TR 178 showed an impressive 171-fold increase in FRET; the increase in FRET observed with His-BTK was only 28-fold (FIG. 4B). Unlike AF-staur, TR 178 demonstrated a plateau at high concentrations with both BTK-Btn and His-BTK permitting analysis of the dose-response curve to measure EC50 values (Table 2).

TABLE 2

Fold FRET increase upon binding of kinases to tracers

| protein | ligand | Max FRET increase | $EC_{50}$ (nM) |
|---|---|---|---|
| BTK-Btn | AF647-staur | 49-fold | nd |
| His-BTK | AF647-staur | 16-fold | nd |
| BTK-Btn | TR 178 | 171-fold | 2.95 ± 0.19 |
| His-BTK | TR 178 | 28-fold | 0.35 ± 0.08 |
| ITK-Btn | AF647-staur | 21-fold | nd |
| GST-ITK | AF647-staur | 7-fold | nd |
| ITK-Btn | TR 236 | 17-fold | nd |
| GST-ITK | TR 236 | 4-fold | nd |
| Jak3 KD-Btn | AF647-staur | 49-fold | 2.89 ± 0.25 |
| GST-Jak3 KD | AF647-staur | 10-fold | 0.83 ± 0.05 |
| Jak3 KD-Btn | TR 236 | 63-fold | 11.1 ± 1.3 |
| GST-Jak3 KD | TR 236 | 26-fold | 2.13 ± 0.14 |

Max FRET increase was measured at 30 nM tracer and 5 nM kinase. nd, not determined.

TR-FRET Assay with ITK and Jak3 KD

Would kinases other than BTK show a larger increase in FRET using C-terminal biotinylation rather than N-terminal tagging? We next studied IL-2-inducible T cell kinase (ITK) (19). ITK containing either a C-terminal Bioease tag (ITK-Btn) or N-terminal GST tag (GST-ITK) was obtained, and the kinases were titrated with AF647-staur from 0.01 nM to 30 nM. The increase in FRET was determined to be 21-fold for ITK-Btn and 7-fold for GST-ITK (FIG. 5A). We also characterized ITK utilizing a second tracer molecule, TR 236 (TR 178 showed minimal signal change with ITK). TR 236 showed a FRET increase that was similar to AF-staur for both ITK-Btn and GST-ITK (FIG. 5B). Neither AF647-staur nor TR 236 demonstrated a plateau in dose-response at 30 nM tracer.

To explore if another kinase also shows a stronger FRET signal with C-terminal biotinylation compared to N-terminal tagging, the tyrosine kinase Jak3 was studied (20). Jak3 is a multi-domain protein, but in these experiments the isolated kinase domain (Jak3 KD) was examined. Jak3 KD containing either a C-terminal Bioease tag (Jak3 KD-Btn) or an N-terminal GST tag (GST-Jak3 KD) was studied. Titrating Jak3 KD-Btn and GST-Jak3 KD with AF647-staur provided a maximal fold increase of 49-fold and 10-fold, respectively (FIG. 5C). Fitting the dose-response curve provided an $EC_{50}$ of 2.89±0.25 for Jak3 KD-Btn and 0.83±0.05 nM for GST-Jak3 KD. The binding of Jak3 KD to TR 236 was also studied. Here, a maximal fold increase of 63-fold and 26-fold was observed for Jak3 KD-Btn and GST-Jak3 KD, respectively (FIG. 5D); the $EC_{50}$ values were 11.1±1.3 for Jak3 KD-Btn and 2.13±0.14 nM for GST-Jak3 KD. Like ITK, Jak3 KD did not demonstrate a strong signal change with TR 178.

Optimization of TR-FRET Assay with BTK-Btn and TR 178

Figure 6:
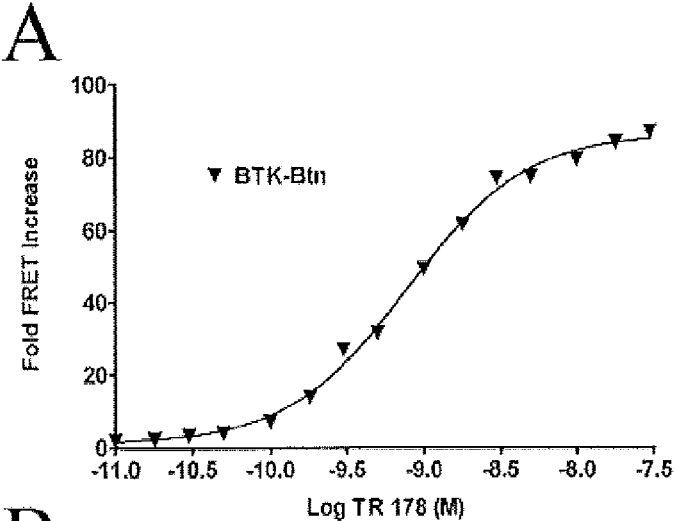
FIG. 6 Optimization of the FRET signal using BTK-Btn and TR 178. (A) Shown is the Fold FRET Increase for BTK-Btn as a function of TR 178 at 0.5 nM BTK-Btn. (B) Potency of BTK inhibitors using BTK-Btn and TR 178 at [TR 178] =0.05 nM. Shown is the percent of maximal FRET (7-fold over baseline in this experiment) as a function of compound concentration. Solid lines represent the nonlinear least squares best fit to a sigmoidal dose-response function. Here, [Btn-BTK]=0.5 nM. IC50 values are shown in Table 3. (C) Potency of BTK inhibitors using BTK-Btn and TR 178 at [BTK-Btn]=0.05 nM. Shown is the percent of maximal FRET (5.5-fold over baseline in this experiment) as a function of compound concentration. Solid lines represent the nonlinear least squares best fit to a sigmoidal dose-response function. Here, [TR 178]=0.5 nM.
Figure 6:
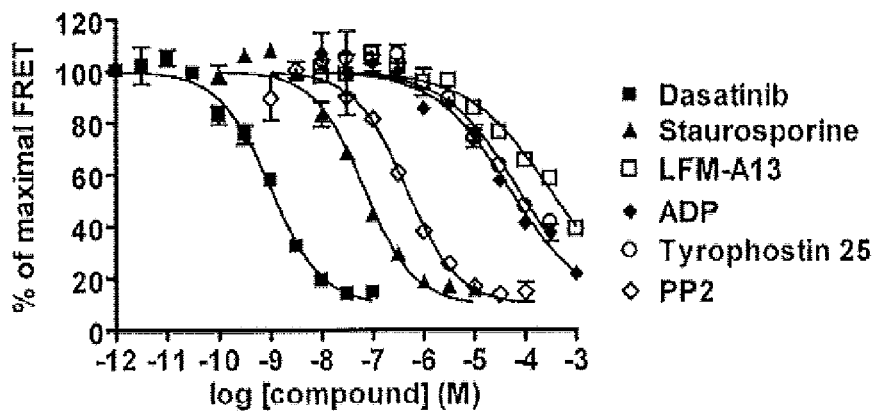
Figure 6:
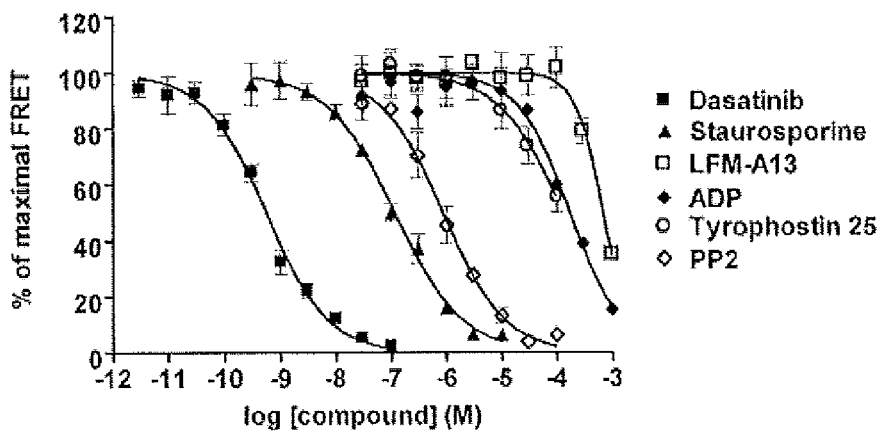

The stronger FRET signal observed upon binding of TR 178 to Btn-BTK compared to AF647-staur (See FIGS. 4A and 4B) focused attention on the BTK-Btn/TR 178 combination for further optimization of the TR-FRET assay for BTK. Titration of TR 178 with BTK-Btn revealed a $K_d$ for this interaction of 0.75±0.11 nM (FIG. 6A). We focused on determining assay conditions that would minimize either the concentration of TR 178 or BTK-Btn since these conditions would facilitate high throughput screening or assessment of potency for strong BTK inhibitors, respectively. It was determined that a concentration of only 50 µM TR 178 (together with 0.5 nM [BTK-Btn]) provided a 7-fold FRET increase, which would be more than ample for high-throughput screening (FIG. 6B). Furthermore, only 50 µM of BTK-Btn (together with 0.5 nM [TR 178]) was required to provide an ample FRET increase of 5.4-fold (FIG. 6C) for assessment of very potent compounds. Compound IC50s determined with these conditions were close to IC50s determined using higher concentrations of BTK-Btn and AF647-staur (Tables 1 and 3). These optimization experiments reveal that tagging BTK with biotin at its C-terminus provides a FRET-based binding assay with superior sensitivity, enabling improved high-throughput screening and better assessment of potency for strong BTK inhibitors.

TABLE 3

Potency of BTK inhibitors measured by FRET competition under low tracer and low kinase conditions.

| compound | Low tracer $IC_{50}$ (µM) | Low tracer $n_H$ | Low kinase $IC_{50}$ (µM) | Low kinase $n_H$ |
|---|---|---|---|---|
| dasatinib | 0.0005 ± 0.0001 | 0.9 ± 0.1 | 0.0006 ± 0.0001 | 0.8 ± 0.1 |
| staurosporine | 0.056 ± 0.009 | 0.9 ± 0.1 | 0.12 ± 0.02 | 0.8 ± 0.1 |
| LFM-A13 | 240 ± 30 | 0.6 ± 0.2 | 700 ± 100 | 1.3 ± 0.1 |
| ADP | 40 ± 11 | 0.7 ± 0.2 | 200 ± 40 | 0.9 ± 0.1 |
| Tyrphostin 25 | 45 ± 9 | 0.6 ± 0.2 | 130 ± 10 | 0.8 ± 0.1 |
| PP2 | 0.32 ± 0.09 | 0.9 ± 0.1 | 0.86 ± 0.15 | 1.8 ± 0.1 |

Low tracer conditions are 0.05 nM TR 178 and 0.5 nM BTK-Btn. Low kinase conditions are 0.05 nM BTK-Btn and 0.5 nM TR 178. $n_H$, hill slope of dose response curve. nd, not determined.

References

1. Singh, P., and Ward, W. H. J. (2008) Alternative assay formats to identify diverse inhibitors of protein kinases. *Expert Opin. Drug Discov.* 3, 819-831.
2. Cohen, P. (2002) Protein kinases—the major drug targets of the twenty-first century? *Nat Rev Drug Discov.* 1, 309-15.
3. Noble, M. E., Endicott, J. A., and Johnson, L. N. (2004) Protein kinase inhibitors: insights into drug design from structure. *Science.* 303, 1800-5.
4. Chene, P. (2008) Challenges in design of biochemical assays for the identification of small molecules to target multiple conformations of protein kinases. *Drug Discov Today.* 13, 522-9.
5. Barr, R. K., Boehm, I., Attwood, P. V., Watt, P. M., and Bogoyevitch, M. A. (2004) The critical features and the mechanism of inhibition of a kinase interaction motif-based peptide inhibitor of JNK. *J Biol Chem.* 279, 36327-38.
6. Okram, B., Nagle, A., Adrian, F. J., Lee, C., Ren, P., Wang, X., Sim, T., Xie, Y., Wang, X., Xia, G., Spraggon, G., Warmuth, M., Liu, Y., and Gray, N. S. (2006) A general strategy for creating "inactive-conformation" abl inhibitors. *Chem Biol.* 13, 779-86.
7. Bogoyevitch, M. A., and Fairlie, D. P. (2007) A new paradigm for protein kinase inhibition: blocking phosphorylation without directly targeting ATP binding. *Drug Discov Today.* 12, 622-33.
8. Liu, Y., and Gray, N. S. (2006) Rational design of inhibitors that bind to inactive kinase conformations. *Nat Chem Biol.* 2, 358-64.
9. Lebakken, C. S., Hee Chol, K., and Vogel, K. W. (2007) A fluorescence lifetime based binding assay to characterize kinase inhibitors. *J Biomol Screen.* 12, 828-41.
10. Kashem, M. A., Nelson, R. M., Yingling, J. D., Pullen, S. S., Prokopowicz, A. S., 3rd, Jones, J. W., Wolak, J. P., Rogers, G. R., Morelock, M. M., Snow, R. J., Homon, C. A., and Jakes, S. (2007) Three mechanistically distinct kinase assays compared: Measurement of intrinsic ATPase activity identified the most comprehensive set of ITK inhibitors. *J Biomol Screen.* 12, 70-83.
11. Smith, C. K., and Windsor, W. T. (2007) Thermodynamics of nucleotide and non-ATP-competitive inhibitor binding to MEK1 by circular dichroism and isothermal titration calorimetry. *Biochemistry.* 46, 1358-67.
12. Takeda, H., Fukumoto, A., Miura, A., Goshima, N., and Nomura, N. (2006) High-throughput kinase assay based on surface plasmon resonance suitable for native protein substrates. *Anal Biochem.* 357, 262-71.
13. Zhang, W. X., Wang, R., Wisniewski, D., Marcy, A. I., LoGrasso, P., Lisnock, J. M., Cummings, R. T., and Thompson, J. E. (2005) Time-resolved Forster resonance energy transfer assays for the binding of nucleotide and protein substrates to p38alpha protein kinase. *Anal Biochem.* 343, 76-83.
14. Lebakken, C., Riddle, S., Singh, U., Frazee, J., Eliason, H., Wolken, J., Gao, Y., Reichling, L., Marks, B., Hereley, S., Leathers, R., and Vogel, K. W. (2008) A One-step, Mix-and-Read, TR-FRET Binding Assay to Characterize Kinase Inhibitors. *MipTec Meeting, Oct.* 14-16, 2008, Basel, Switzerland.
    http://tools.invitrogen.com/content/sfs/posters/A-binding-assay-to-characterize-kinase-inhibitors.pdf
15. Tirat, A., Freuler, F., Stettler, T., Mayr, L. M., and Leder, L. (2006) Evaluation of two novel tag-based labelling technologies for site-specific modification of proteins. *Int J Biol Macromol.* 39, 66-76.
16. Hantschel, O., Rix, U., Schmidt, U., Burckstummer, T., Kneidinger, M., Schutze, G., Colinge, J., Bennett, K. L., Ellmeier, W., Valent, P., and Superti-Furga, G. (2007) The Btk tyrosine kinase is a major target of the Bcr-Abl inhibitor dasatinib. *Proc Natl Acad Sci USA.* 104, 13283-8.
17. Dinh, M., Grunberger, D., Ho, H., Tsing, S. Y., Shaw, D., Lee, S., Barnett, J., Hill, R. J., Swinney, D.C., and Bradshaw, J. M. (2007) Activation mechanism and steady state kinetics of Bruton's tyrosine kinase. *J Biol Chem.* 282, 8768-76.
18. Mahajan, S., Ghosh, S., Sudbeck, E. A., Zheng, Y., Downs, S., Hupke, M., and Uckun, F. M. (1999) Rational design and synthesis of a novel anti-leukemic agent targeting Bruton's tyrosine kinase (BTK), LFM-A13 [alpha-cyano-beta-hydroxy-beta-methyl-N-(2,5-dibromophenyl) propenamide]. *J Biol Chem.* 274, 9587-99.
19. Kosaka, Y., Felices, M., and Berg, L. J. (2006) Itk and Th2 responses: action but no reaction. *Trends Immunol.* 27, 453-60.
20. Papageorgiou, A. C., and Wikman, L. E. (2004) Is JAK3 a new drug target for immunomodulation-based therapies? *Trends Pharmacol Sci.* 25, 558-62.
21. Huse, M., and Kuriyan, J. (2002) The conformational plasticity of protein kinases. *Cell.* 109, 275-82.
22. Mol, C. D., Fabbro, D., and Hosfield, D. J. (2004) Structural insights into the conformational selectivity of STI-571 and related kinase inhibitors. *Curr Opin Drug Discov Devel.* 7, 639-48.
23. Lackey, K. E. (2006) Lessons from the drug discovery of lapatinib, a dual ErbB1/2 tyrosine kinase inhibitor. *Curr Top Med Chem.* 6, 435-60.

What is claimed:

1. A method of screening for a substance that may be acting as a kinase inhibitor, said method comprising the steps of:
   a) providing a kinase enzyme that is fused at its C-terminus with an amino acid sequence that allows covalent attachment of biotin wherein said amino acid sequence comprises SEQ ID NO:1;
   b) providing streptavidin that is labeled with a fluorescent donor moiety or a fluorescent acceptor moiety;
   c) providing a known kinase inhibitor wherein said known kinase inhibitor is labeled with a fluorescent acceptor moiety if said streptavidin in step b) is labeled with a fluorescent donor moiety, and wherein said known kinase inhibitor is labeled with a fluorescent donor moiety if said streptavidin in step b) is labeled with a fluorescent acceptor moiety;
   d) incubating said kinase enzyme, said streptavidin and said known kinase inhibitor in a reaction mixture in either the presence or absence of said substance;
   e) exposing the reaction mixture to light that allows fluorescence resonance energy transfer to take place and measuring fluorescence emission from the reaction mixture; wherein if the fluorescence emission measurement from the reaction mixture in the presence of said substance is different than the fluorescent emission measurement from the mixture in the absence of said substance, said substance is acting as a kinase inhibitor.

2. The method of claim 1 wherein the covalent attachment of biotin occurs intracellularly.

3. The method of claim 1 wherein the covalent attachment of biotin occurs in vitro.

* * * * *

SEQUENCE LISTING

<160> NUMBER OF SEQ ID NOS: 2

<210> SEQ ID NO 1
<211> LENGTH: 72
<212> TYPE: PRT
<213> ORGANISM: Klebsiella pneumoniae

<400> SEQUENCE: 1

Gly Ala Gly Thr Pro Val Thr Ala Pro Leu Ala Gly Thr Ile Trp Lys
1               5                   10                  15

Val Leu Ala Ser Glu Gly Gln Thr Val Ala Ala Gly Glu Val Leu Leu
            20                  25                  30

-continued

```
Ile Leu Glu Ala Met Lys Met Glu Thr Glu Ile Arg Ala Ala Gln Ala
            35                  40                  45
Gly Thr Val Arg Gly Ile Ala Val Lys Ala Gly Asp Ala Val Ala Val
        50                  55                  60
Gly Asp Thr Leu Met Thr Leu Ala
65                  70

<210> SEQ ID NO 2
<211> LENGTH: 13
<212> TYPE: PRT
<213> ORGANISM: Escherichia coli

<400> SEQUENCE: 2

Asn Asp Ile Phe Glu Ala Gln Lys Ile Glu Trp His His
1               5                   10
```